United States Patent
Grams

[11] Patent Number: 5,968,008
[45] Date of Patent: Oct. 19, 1999

[54] CANNULA WITH PARALLEL CHANNELS AND SLIDING SHEATH

[76] Inventor: Guenter A. Grams, 2443 Norse Ave., Costa Mesa, Calif. 92627

[21] Appl. No.: 08/905,753

[22] Filed: Aug. 4, 1997

[51] Int. Cl.[6] ..................................................... A61M 1/00
[52] U.S. Cl. ............................... 604/35; 604/27; 604/264
[58] Field of Search .................................. 604/35, 27, 39, 604/40, 43, 45, 54, 264, 268, 93

[56] References Cited

U.S. PATENT DOCUMENTS

| | | | |
|---|---|---|---|
| 4,014,333 | 3/1977 | McIntyre | 128/240 |
| 5,160,319 | 11/1992 | Emery et al. | 604/27 |
| 5,163,433 | 11/1992 | Kagawa et al. | 128/660.01 |
| 5,379,773 | 1/1995 | Hornsby | 128/662.06 |
| 5,718,668 | 2/1998 | Arnett et al. | 601/155 |
| 5,738,648 | 4/1998 | Lands et al. | 604/35 |
| 5,827,218 | 10/1998 | Nguyen et al. | 604/30 |
| 5,846,219 | 12/1998 | Vancaillie | 604/35 |

*Primary Examiner*—Corrine McDermott
*Assistant Examiner*—Cris L. Rodriguez
*Attorney, Agent, or Firm*—Price, Gess & Ubell

[57] ABSTRACT

An improved cannula having parallel conduits, one for removing material and one for injecting material, is disclosed. In certain medical procedures, it is necessary to deposit fluid while simultaneously withdrawing material in the same region. The present invention is designed to serve this task. The improved cannula of the present invention further features a sheath mounted on a needle for slidable movement therealong to facilitate the maneuvers required to perform the procedures. The cannula comprises a handle that includes a nozzle at one end which conveniently connects to a vacuum pump. The needle is connected to the handle and includes a plurality of apertures at a tip. A first conduit is formed from the apertures along the lumen of the needle through the handle and to the vacuum pump. Once the needle is inserted into a patient, the first conduit communicates the vacuum to a subdermal region which results in the removal of material therein. Simultaneously, a second conduit in the form of a capillary tube within the first conduit inserts fluid through a separate outlet into the same subdermal region. Alternatively, a second conduit can be formed in the annular region between the sheath and the needle to dispense the fluid into the subdermal region.

8 Claims, 3 Drawing Sheets

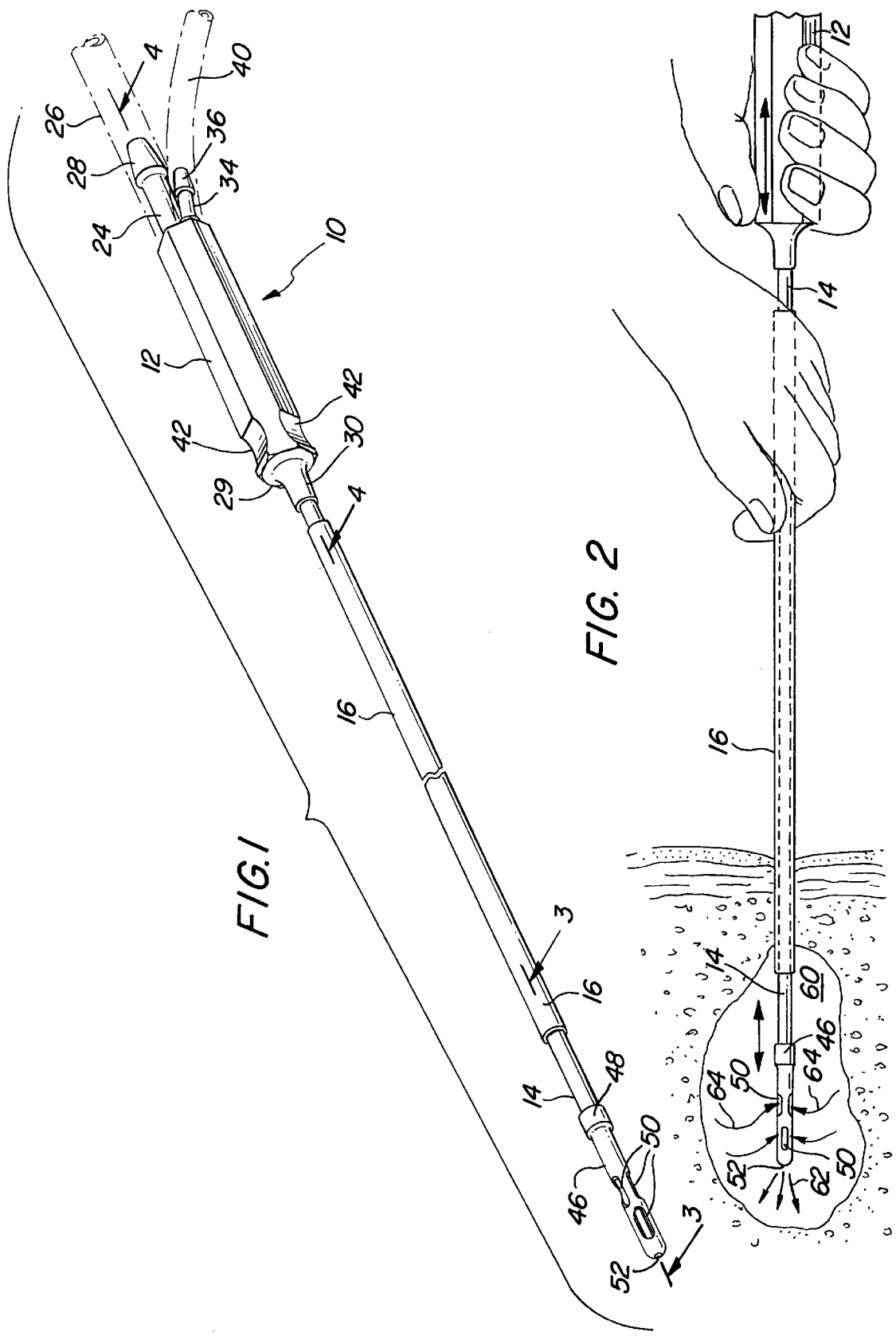

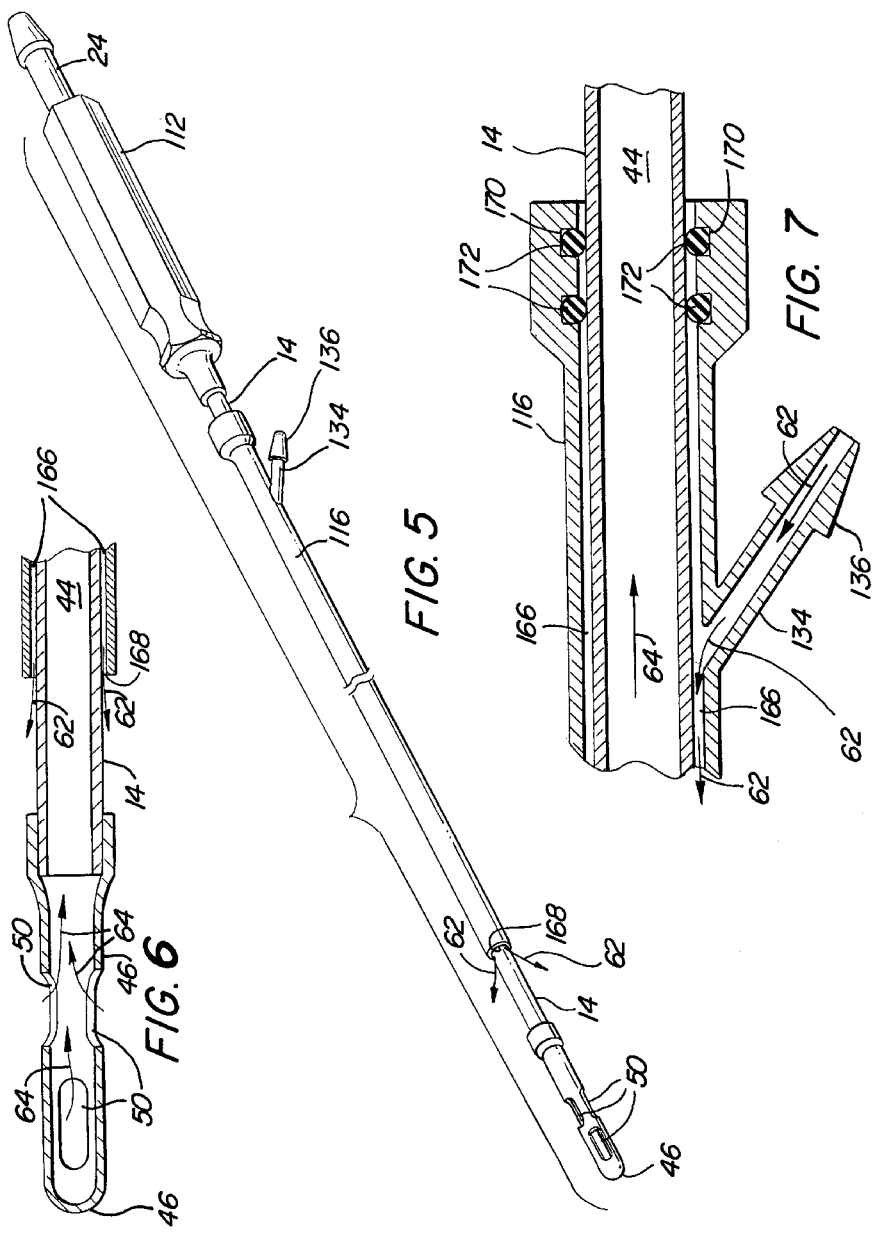

5,968,008

CANNULA WITH PARALLEL CHANNELS AND SLIDING SHEATH

BACKGROUND OF THE INVENTION

1. Field of the Invention

The present invention relates to cannulas, and in particular to a cannula with two distinct channels, one dedicated to the removal of material from a subdermal region and one dedicated to the injection of fluid into the subdermal region whereby the removal and the injection can occur simultaneously.

2. Description of Related Art

Lipectomy is a medical procedure in which fat is removed from a patient using a long cannula connected to a syringe or vacuum pump. Originally, the procedure was performed "dry," in that no fluid was introduced into the targeted area prior to removal of the fat. More recently, doctors have realized that swelling and post-surgery pain can be reduced by initially introducing certain fluids into the region prior to the removal of the fat. The fluids can help break up the fat, making removal easier, and can also deliver anesthetic to the targeted region. This heretofore has been accomplished in two separate steps, the first step being the injection of fluid into the patient and then a second step of removing the fluid and fat from the targeted area. However, the difficulty in this process is that the patient is subjected to multiple injections, and also the fluid is not adequately dispersed in the targeted area. Moreover, the removal of the fat can be a task which requires significant movement of the cannula back and forth as the doctor attempts to reach all parts of the targeted area. The motion of the cannula back and forth often causes trauma to the area such as bruising, which results in a longer recovery period.

What the prior art lacks is a cannula which would permit both fat withdrawal and fluid injection simultaneously, limiting the number of injections that the patient is subjected to while ensuring adequate dispersal of the injected fluid into the targeted region. Ideally, the injection point of the fluid would coincide with the entrance to the channel through which the fat is removed so that the area subjected to the fat removal is guaranteed to also receive adequate exposure to the fluid.

SUMMARY OF THE INVENTION

The shortcomings of the prior art are overcome by the present invention, which includes a cannula with two separate, parallel channels, one for extraction and another for injection, located within a sliding sheath. In a first embodiment, an extraction channel travels from an opening at the tip of the cannula through the lumen, into the handle and out a nozzle which is connected to a vacuum pump. An injection channel is formed by an annular region between the sheath and the cannula, or alternatively by a capillary tube located inside the lumen of the cannula. When the injection channel is formed between the sheath and the cannula, an injection nozzle is mounted directly to the sheath. A seal aft of the injection nozzle causes the fluid to be directed out of the distal end of the sheath. When the capillary tube is used as the injection channel, it is preferably accessed through an injection nozzle located on the cannula handle. The injection nozzle in both embodiments are connected to a pressurized fluid source. Fat or other material to be removed is vacuumed through the extraction channel by the vacuum pump and thereby removed from the body, while fluid is introduced through the injection channel into the area from which the material is being removed.

BRIEF DESCRIPTION OF THE DRAWINGS

The exact nature of this invention, as well as its objects and advantages, will become readily apparent upon reference to the following detailed description when considered in conjunction with the accompanying drawing, wherein:

FIG. 1 is a perspective view of a first embodiment of the present invention;

FIG. 2 is side view demonstrating the operation of the embodiment of FIG. 1;

FIG. 5 is a perspective view of a second embodiment of the present invention;

FIG. 6 is a cross-sectional view of the end of the cannula and tip of the embodiment of FIG. 5; and FIG. 7 is a cross-sectional view of the sheath with nozzle and seal of the embodiment of FIG. 5.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a cannula with parallel channels and a slidable sheath.

Figure 3:
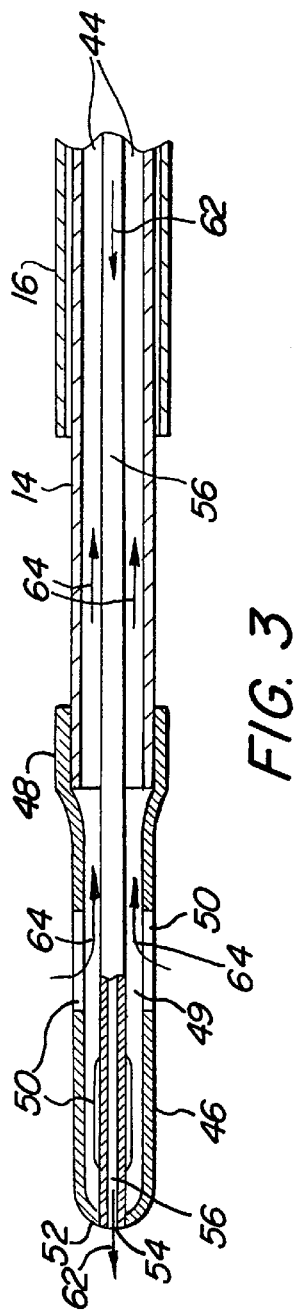
FIG. 3 is a cross-sectional view of the end of the cannula and tip of the embodiment of FIG. 1.
Figure 4:
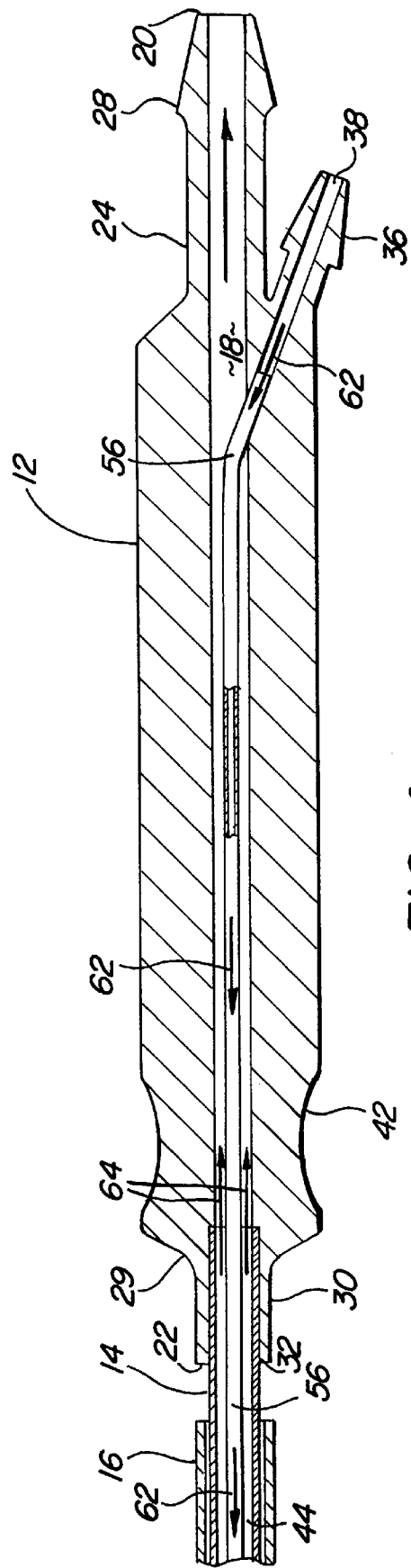
FIG. 4 is a cross-sectional view of the handle of the embodiment of FIG. 1.

A first embodiment of the present invention is generally illustrated in FIGS. 1 through 4. A cannula 10 includes a handle or base 12, a hollow rod or needle 14, and a sheath 16. The handle 12, shown in cross-section in FIG. 4, has a channel 18 extending longitudinally from a first end 20 to a second end 22. The handle includes a nozzle 24 at the first end 20 which is adapted to fit inside a tube 26. The tapered head 28 of the nozzle helps to prevent the tube 26 from becoming dislodged during the procedure. At the second end 22 of the handle 12, a shoulder 29 narrowing to a neck 30 is provided which terminates at the mouth 32 of the channel 18 which is also the first stop for limiting lateral movement of sheath 16. At a rear portion of the handle 12 is a second nozzle 34 having a tapered head 36. The nozzle 34 is aligned with a smaller channel 38 which extends to the larger channel 18, and the nozzle 34 is inclined to reduce the included angle between the two channels. The small nozzle 34 is sized to fit snugly inside tube 40, with the tapered head 36 helping to retain the tube 40 on the nozzle 34.

The handle's exterior includes recesses 42 at the front end which are formed to receive the user's thumb for greater comfort and control of the cannula 10. Although a hexagonal profile is shown, the profile may be any ergonomical shape which provides traction and may be comfortably gripped for extended periods of time.

Connected to the handle 12 is a hollow rod or needle 14 which fits into the mouth 32 of the channel 18 and is preferably welded or glued for a permanent connection. The needle 14 has a lumen 44 which extends along the length of the needle 14 and is in communication with the channel 18 when the needle 14 is secured to the handle 12. At the distal end of the needle 14 (see FIG. 3), a tip 46 is provided which is placed over the end of the needle 14 and permanently secured thereon. The tip 46 has a collar end 48 which receives the end of the needle and a cavity 49 which is exposed through circumferentially spaced openings 50 at an opposite end of the tip 46. At the head 52 of the tip 46 is a hole 54 aligned with the channel 18. The collar end 48 serves as the second stop for the sheath 16.

A capillary tube 56 located inside the lumen 44 of the needle provides the cannula's second channel. The capillary tube 56 is connected from the nozzle 34 to the hole 54 at the head of the tip 46. The capillary tube 56 forms one conduit between the end of the cannula and the handle 12, and the cavity 49, lumen 44, and channel 18 form a second continuous conduit between the end of the cannula and the handle 12. In a preferred embodiment, a cylindrical sheath 16 is placed over the needle 14, where the length of the sheath 16 is less than the length of the needle 14 between the mouth 32 of the handle 12 and the collar end 48 of the tip 46. Having a shorter length allows the sheath 16 to slide between these two positions, a feature whose advantages are explained below.

The operation of the cannula 10 of the first embodiment will now be described with reference to FIG. 2. The handle 12 is grasped by the user in one hand with the thumb disposed in the recess 42. The needle 14 is placed through an incision in the patient and inserted into the subdermal region 60 where fat is located. Nozzle 34 is connected to tube 40 which feeds the pre-selected fluid (indicated by arrows 62) into the capillary tube 56, where it is eventually expelled out hole 54. Simultaneously, nozzle 24 is connected via tube 26 to a pumping apparatus (not shown) and the resulting vacuum is communicated through the handle channel 18, the needle lumen 44, and the tip cavity 49. Material comprised of fat and fluid (indicated by arrows 64) adjacent the tip openings 50 is sucked through the openings 50, down the lumen 44, through the handle 12 and out the nozzle 24 where the pumping apparatus (not shown) deposits the material in a reservoir. The proximity of the fluid outlet 54 and the inlet 50 for the material 64 allows the region 60 to be injected and vacuumed simultaneously. With the sheath 16 held stationary by the user's second hand, the needle 14 can be thrust back and forth without the patient experiencing the rubbing of the needle 14 through the incision and the inherent detrimental effects thereof. The first stop 32 at handle 12, and the second stop 48 at the distal end of the needle, or hollow rod 14, define a linear path of travel for the sheath 16 on the rod 14 when the sheath is held stationary.

A second embodiment illustrated in FIGS. 5 through 7 will now be described, with elements identical to the first described embodiment having like reference numbers. Handle 112 is similar to the previous handle sans the second nozzle projecting from the side and associated channel, but includes the nozzle 24 at the end and is otherwise identical. Similarly, needle 14 and tip 46 are as described previously, although the lumen 44 of the needle 14 is unoccupied. The sheath 116 of the second embodiment is once again sized to fit over the needle 14 in a sliding manner between the handle 112 and the tip 46 as described above. Sheath 116 is provided with a nozzle 134 including a tapered head 136 which mates with a tube to perform the same function as the first embodiment. As shown in FIG. 7, the second channel 166 is defined as an annular duct between the sheath 116 and the needle 14 which extends along the interior length of the sheath 116. Fluid (depicted as arrows 62) introduced into the second channel 166 travels the length of the channel 166 and is expelled at outlet 168, which is in proximity with the openings 50 of the tip 46. To prevent fluid from exiting the rear of the channel 166, the sheath includes annular grooves 170 which hold sealing rings 172. The sealing rings 172 prevent the fluid from escaping the rear of the channel 166, thereby forcing the fluid out of the outlet 168, without significantly interfering with the sliding characteristic of the sheath 116. Thus, as before the fluid is transmitted to the subdermal region in proximity with the inlet of tip 46 where material is removed. In both embodiments, a parallel channel is provided to permit simultaneous fluid injection and material withdrawal, and a sliding sheath protects the patient from unnecessary trauma due to the often vigorous motion of the needle through the incision.

It will be understood that the embodiment described herein are merely exemplary and that a person skilled in the art may make many variations and modifications without departing from the spirit and scope of the invention. All such variations and modifications are intended to be included within the scope of the invention as defined in the appended claims.

What is claimed is:

1. A cannula comprising:

a hollow elongated rod having a distal end and a proximal end with an opening at each end forming a first channel:

a sheath slidably mounted on the elongated hollow rod;

a handle mounted to said hollow rod, the handle including a first stop adjacent the proximal end of the elongated rod, and the distal end of the rod includes a second stop, the first and second stops defining a linear path of travel for the sheath; and means for introducing a vacuum into the first channel.

2. The cannula of claim 1 further comprising a second channel formed by a capillary tube inside the first channel, the capillary tube extending from an inlet at the proximal end to the outlet at the distal end of the hollow rod.

3. The cannula of claim 1, further comprising a second channel formed by an annular duct between the hollow rod and said sheath.

4. The improved cannula of claim 1 wherein the handle has a hexagonal profile with a recessed region adjacent a first end sized to receive a thumb.

5. The improved cannula of claim 1 wherein the distal end of the hollow rod an attached tip and a plurality of openings circumferentially spaced about said attached tip.

6. A bi-channel cannula for injecting fluid into a subdermal region and simultaneously removing material from the subdermal region comprising:

a hollow base having a nozzle at a first end in communication with a channel extending to a second end;

a needle having a distal end and a proximal end, the distal end including a tip with an aperture, the proximal end connected to the second end of the base such that a lumen of the needle and the channel form a conduit from the aperture at the tip of the needle to the nozzle of the base;

a capillary tube disposed within the conduit having an inlet at the base and an outlet at the tip of the needle;

a slidable sheath disposed about the shaft between the distal and proximal ends; and the hollow base including a first stop adjacent the proximal end of the needle, and the distal end of the needle including a second stop, the first and second stops defining a linear path of travel for the sheath.

7. The cannula of claim 6 wherein the base has a hexagonal profile with a recessed area at the second end sized to receive a thumb.

8. The cannula of claim 6 wherein the tip includes a plurality of apertures circumferentially spaced thereabout.

\* \* \* \* \*